(12) United States Patent
McSweeney (10) Patent No.: US 10,411,404 B2
(45) Date of Patent: Sep. 10, 2019

(54) GROOVED CONNECTOR WITH LAND BRIDGE

(71) Applicant: HeartWare, Inc., Miami Lakes, FL (US)

(72) Inventor: Timothy McSweeney, South Miami, FL (US)

(73) Assignee: HeartWare, Inc., Miami Lakes, FL (US)

(*) Notice: Subject to any disclaimer, the term of this patent is extended or adjusted under 35 U.S.C. 154(b) by 0 days.

(21) Appl. No.: 16/201,131

(22) Filed: Nov. 27, 2018

(65) Prior Publication Data

US 2019/0097353 A1 Mar. 28, 2019

Related U.S. Application Data

(63) Continuation of application No. 15/794,127, filed on Oct. 26, 2017, now Pat. No. 10,158,195.

(Continued)

(51) Int. Cl.
*H01R 13/629* (2006.01)
*H01R 13/639* (2006.01)
*H01R 24/00* (2011.01)
*A61M 1/10* (2006.01)
*A61M 1/12* (2006.01)

(Continued)

(52) U.S. Cl.
CPC .......... *H01R 13/629* (2013.01); *A61M 1/101* (2013.01); *A61M 1/122* (2014.02); *H01R 9/22* (2013.01); *H01R 13/639* (2013.01); *H01R 24/005* (2013.01); *A61M 1/127* (2013.01); *H01R 13/6271* (2013.01); *H01R 13/635* (2013.01)

(58) Field of Classification Search
CPC ..... H01R 13/6271; H01R 13/629; H01R 9/22
See application file for complete search history.

(56) References Cited

U.S. PATENT DOCUMENTS 2,869,099 A 1/1959 Robinson
3,671,921 A 6/1972 Baker, III et al.
(Continued)

FOREIGN PATENT DOCUMENTS

EP 2355553 A1 8/2011

OTHER PUBLICATIONS

International Search Report and Written Opinion dated Jan. 22, 2018, for corresponding International Application No. PCT/US2017/058403, International Filing Date: Oct. 26, 2017 consisting of 12 pages.

*Primary Examiner* — Briggitte R. Hammond
(74) *Attorney, Agent, or Firm* — Christopher & Weisberg, P.A.

(57) ABSTRACT

A connector assembly including a female element having a bore with an open end. A male element is insertable into the bore of the female element along an axis in a first axial direction and removable from the bore of the female element in a second axial direction. One of the female and male elements defines a circumferential surface extending around the axis and a depression in the circumferential surface, the depression having a catch wall facing in one of the first and second axial directions and a release wall facing in the other one of the first and second axial directions. A second one of the male and female elements has a finger mounted thereon, the finger has a catch end biased in a radial direction transverse to the axis, the catch end of the finger being configured to engage the depression and abut the catch wall.

17 Claims, 7 Drawing Sheets

Related U.S. Application Data

(60) Provisional application No. 62/413,123, filed on Oct. 26, 2016.

(51) Int. Cl.
   *H01R 13/627* (2006.01)
   *H01R 13/635* (2006.01)
   *H01R 9/22* (2006.01)

(56) References Cited

U.S. PATENT DOCUMENTS

| | | |
|---|---|---|
| 4,810,214 A | 3/1989 | Yohn |
| 5,885,280 A | 3/1999 | Nettekoven et al. |
| 7,628,632 B2 | 12/2009 | Holland |
| 9,136,643 B2 | 9/2015 | Behning |
| 2015/0222050 A1 | 8/2015 | Behning |
| 2015/0374892 A1 | 12/2015 | Yanai et al. |
| 2016/0340805 A1 | 11/2016 | Nimmo, Sr. |

GROOVED CONNECTOR WITH LAND BRIDGE

CROSS-REFERENCE TO RELATED APPLICATION

This application is a Continuation of U.S. patent application Ser. No. 15/794,127, filed Oct. 26, 2017, and is related to and claims priority to U.S. Provisional Patent Application Ser. No. 62/413,123, filed Oct. 26, 2016, entitled GROOVED CONNECTOR WITH LAND BRIDGE, the entirety of which are incorporated herein by reference.

STATEMENT REGARDING FEDERALLY SPONSORED RESEARCH OR DEVELOPMENT n/a

TECHNICAL FIELD

The present invention generally relates to components for a connector assembly and methods used for connecting and disconnecting a connector assembly.

BACKGROUND

A connector assembly usually includes male and female elements. When coupled together, the elements may, for example, form an electrical connection. In some medical applications, a connector assembly is used with a ventricular assist device (VAD) to connect an electrical cable between a pump incorporated in the VAD and a control unit.

There can sometimes be "push back" at a connection point which over time may cause intermittent connection or accidental disconnection. There may also be some external force opposing the connection, for example, patient movement, that could result in accidental disconnection. In some cases, a small rotation of one of the elements may result in accidental disconnection.

SUMMARY

The present invention advantageously provides a connector assembly including a female element having a bore with an open end. A male element is insertable into the bore of the female element along an axis in a first axial direction and removable from the bore of the female element in a second axial direction opposite the first axial direction. One of the female and male elements defines a circumferential surface extending around the axis and a depression in the circumferential surface, the depression having a catch wall facing in one of the first and second axial directions and a release wall facing in the other one of the first and second axial directions. A second one of the male and female elements has a finger mounted thereon, the finger has a catch end biased in a radial direction transverse to the axis, the catch end of the finger being configured to engage the depression and abut the catch wall to block axial movement of the male element in the second direction relative to the female element when the elements are in a locked position. The male element is movable in the first axial direction relative to the female element to transition from the locked position to an over advanced position, the male and female elements in the over advanced position being rotatable about the axis relative to one another to transition from the over advanced position to an unlocked position.

In another aspect of this embodiment, the depression has side walls and the finger has side edges, wherein the side walls of the depression engage with the side edges of the finger when the elements are in the locked position to maintain the rotational position of the elements relative to each other.

In another aspect of this embodiment, the circumferential surface includes a land bridge offset from the depression in a circumferential direction around the axis and aligned with the depression in the first and second axial directions, and wherein at least one of the male and female elements further includes markings to indicate rotational alignment between the catch end of the finger and the land bridge.

In another aspect of this embodiment, at least one from the group consisting of the male and female elements further includes markings to indicate axial progression during insertion.

In another aspect of this embodiment, the circumferential surface further includes a landing area offset from the depression in an axial direction and disposed adjacent the release wall, the landing area having a first portion aligned with the depression in the circumferential direction and a second portion aligned with the land bridge in the circumferential direction, and wherein the markings further indicate the landing area on the other of the male and female elements.

In another aspect of this embodiment, the connector assembly further includes a spring mounted to one of the male and female elements and engaging the other one of the male and female elements when the male and female are in a range of positions from the locked position to the over advanced position, the spring biasing the male element in the second axial direction.

In another aspect of this embodiment, the female element includes a plurality of depressions in the circumferential surface, and wherein the plurality of depressions are spaced at equal intervals in the circumferential direction and aligned with one another in the axial direction.

In another aspect of this embodiment, the catch wall of the depression and the release wall of the depression are substantially perpendicular to the axis.

In another aspect of this embodiment, the male element includes a plurality of fingers mounted thereon and wherein the number of fingers corresponds to the number of depressions.

In another aspect of this embodiment, the plurality of fingers are spaced at equal intervals in the circumferential direction and aligned with one another in the axial directions.

In another aspect of this embodiment, the finger is resilient and biased by its own resilience.

In another aspect of this embodiment, the bore has a second open end spaced along the axis from the first open end.

In another embodiment, a connector assembly includes a female element having a bore with an open end. A male element is insertable into the bore of the female element along an axis in a first axial direction and removable from the bore of the female element in a second axial direction opposite the first axial direction. The male element defines a circumferential surface extending around the axis and a depression in the circumferential surface, the depression has a catch wall facing in one of the first and second axial directions and a release wall facing in the other one of the first and second axial directions. The female element has a finger mounted thereon the finger having a catch end biased in a radial direction transverse to the axis, the catch end of the finger is configured to engage the depression and abut the catch wall to block axial movement of the male element in the second direction relative to the female element when the elements are in a locked position. The male element is movable in the first axial direction relative to the female element to transition from the locked position to an over advanced position, the male element is removable from the bore of the female element by moving in the second axial direction relative to the female element while the elements are in the unlocked position, the catch end bears on the land bridge during movement in the second axial direction. An electrical contact is disposed on the male element and an electrical contact disposed on the female element, the contact on the male element is engaged with the contact on the female element when the elements are in the locked position.

In another aspect of this embodiment, the catch end of the finger faces the first axial direction and is biased inwardly toward the axis, the catch wall of the depression faces in the second axial direction, and the release wall of the depression facing in the first axial direction.

In another aspect of this embodiment, the circumferential surface includes a land bridge offset from the depression in a circumferential direction around the axis and aligned with the depression in the first and second axial directions.

In another aspect of this embodiment, the circumferential surface further includes a landing area offset from the depression in an axial direction and disposed adjacent the release wall, the landing area having a first portion aligned with the depression in the circumferential direction and a second portion aligned with the land bridge in the circumferential direction.

In another aspect of this embodiment, the catch end of the finger is configured to move over the release wall of the depression onto the first portion of the landing area as the male and female elements transition to the over advanced position, and wherein the male and female elements in the over advanced position being rotatable about the axis relative to one another to transition from the over advanced position to an unlocked position in which the catch end is disposed on the second portion of the landing area, the catch end bearing on the landing area during such rotation.

In another aspect of this embodiment, the landing area is a part of a surface of revolution around the axis.

In another aspect of this embodiment, the circumferential surface is a surface of revolution around the axis.

In another embodiment, a method for releasing a male element and a female element from a locked position includes moving a male element within a bore of a female element in a first axial direction to transition from a locked position, in which a finger on one of the male and female elements is engaged with a depression on the other one of the male and female elements and blocks movement of the male element in a second axial direction opposite the first axial direction, to an over advanced position, the movement in the first axial direction dislodges the finger from the depression and positions the finger on a landing area on the other one of the male and female elements. One of the male and female elements is rotated relative to the other male and female element to transition from the over advanced position to an unlocked position, the rotation moves the finger out of rotational alignment with the depression and aligns the finger with a land bridge on the other one of the male and female elements, the finger bearing on the landing area during rotation. The male element is moved within the bore of the female element in the second axial direction, the finger bearing on the land bridge during as the finger moves past the depression.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
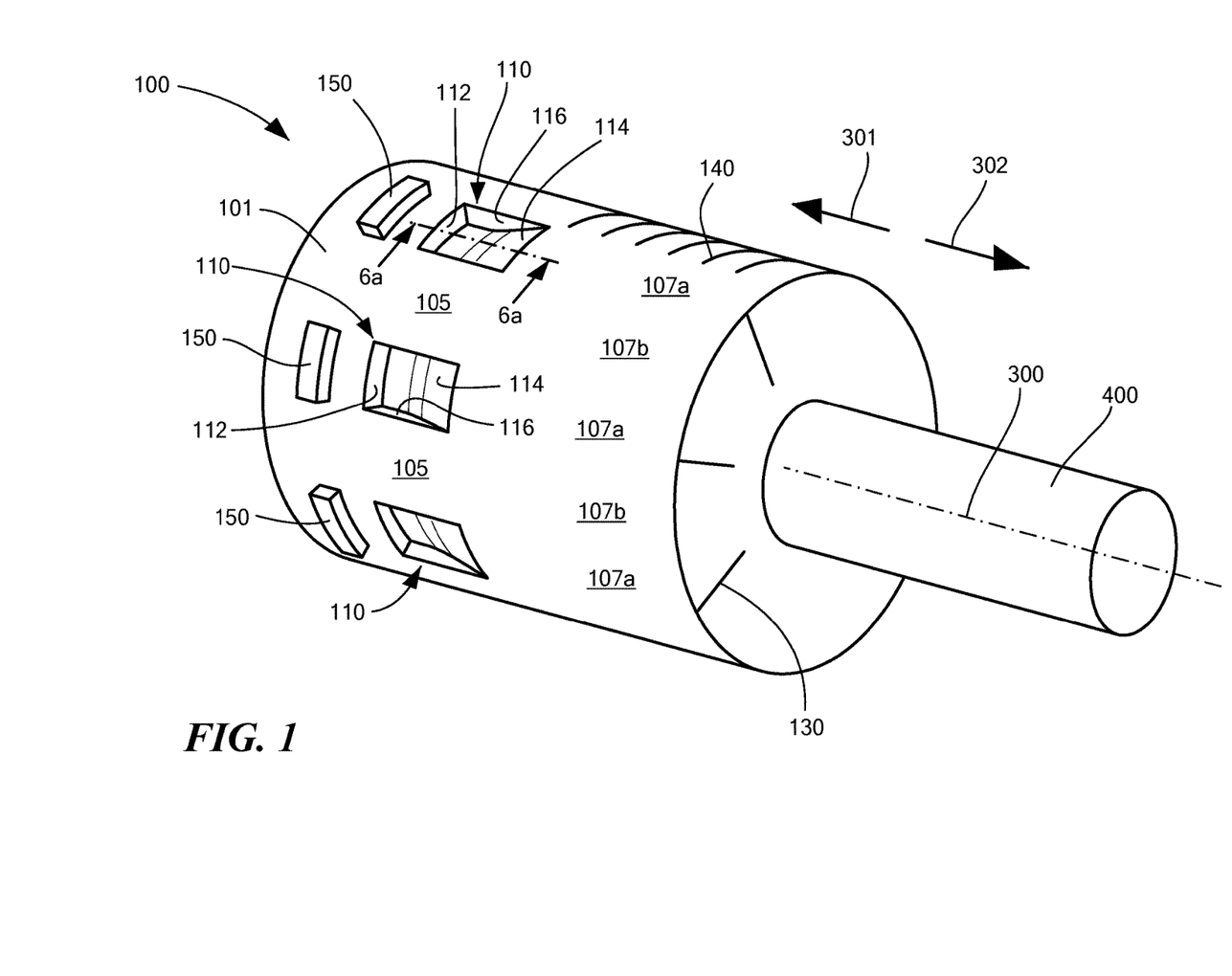
FIG. 1 is a perspective view of one component used in one embodiment of the present disclosure.

Referring now to the drawings in which like reference designators refer to like elements, there is shown in FIG. 1 a male connector of connector assembly according to a first embodiment of the present disclosure and designated generally as "100." The connector assembly includes a male element 100 having a circumferential surface 101 extending around an axis 300. Circumferential surface 101 is a surface of revolution around the axis 300, which is a cylindrical surface in this embodiment. Moreover, axis 300 has a forward or first axial direction 301 and a rearward or second axial direction 302.

Figure 6A:
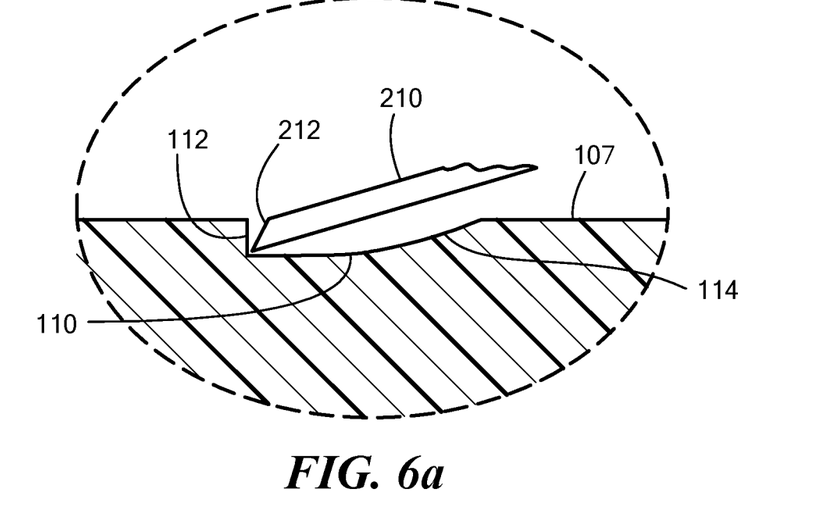
FIG. 6a is a fragmentary sectional view depicting a portion of the component shown in FIG.

Circumferential surface 101 has a plurality of depressions 110 aligned in the axial directions 301,302 and spaced at equal intervals in the circumferential direction around the axis 300. Each depression 110 extends inwardly from the surface of revolution toward axis 300. Each depression has two side walls 116, a catch wall 112 facing the rearward axial direction 302, and a release wall 114 facing the forward axial direction 301. As best seen in FIG. 6a, catch wall 112 is substantially perpendicular to the axis 300 and forms approximately a 90 degree angle with the circumferential surface 101. Release wall 114 slopes outwardly, away from axis 300, in the rearward axial direction 302. The side walls 116 of each depression extend substantially parallel to one another, and are perpendicular or nearly perpendicular to the circumferential surface.

Circumferential surface 101 also has a plurality of land bridges 105 corresponding to the plurality of depressions 110. Land bridges 105 are aligned with the depressions 110 in the axial directions 301, 302 and offset from the depressions 110 in the circumferential direction around the axis 300.

Circumferential surface 101 further includes a plurality of landing areas 107 corresponding to the plurality of depressions 110. Landing areas 107 are offset from the depressions 110 in the rearward axial direction 302 and disposed adjacent the release walls 114. Landing area 107 is also a part of the surface of revolution around the axis 300 defined by circumferential surface 101. Landing area 107 has a first portion 107a aligned with the depression 110 in the circumferential direction around the axis 300 and a second portion 107b aligned with one of the land bridges 105 in the circumferential direction around the axis 300. In this embodiment, the second portion 107b of each landing area is contiguous with the first portion 107a of the next adjacent landing areas, so that all of the landing areas together form a complete surface of revolution around the axis.

As shown in FIG. 1, male element 100 has a set of one or more markings 130. Markings or suitable indicia 130 are disposed at predetermined positions in the circumferential direction relative to the land bridges 105. In this embodiment, each marking 130 is aligned with one of the land bridges 105 in the circumferential direction around the axis 300. Markings 130 can be used to determine the rotational alignment between male element 100 and female element 200, as discussed below. Male element 100 also has a second set of markings 140 to indicate the axial progression of the male element 100 during insertion into female element 200. Markings 140 can be used to determine the axial position of the male element 100 relative to the female element 200.

Additionally, male element 100 includes electrical contacts 150. In this embodiment, contacts 150 are disposed on circumferential surface 101. Male element 100 also has an electrical cable 400 fixed at one end and extending in the rearward axial direction 302. Cable 400 includes conductors (not shown) electrically connected to contacts 150.

The connector assembly according to the first embodiment of the present disclosure further includes a female element 200 (FIGS. 2 and 3) having a housing 220 with internal bore 203 extending along an axis 1300, which is coincident with axis 300 of the male element 100 during operation. The female element 200 has a forward or first axial direction 1301 and a rearward or second axial direction 1302 corresponding with the axial directions 301 and 302 respectively.

Figure 2:
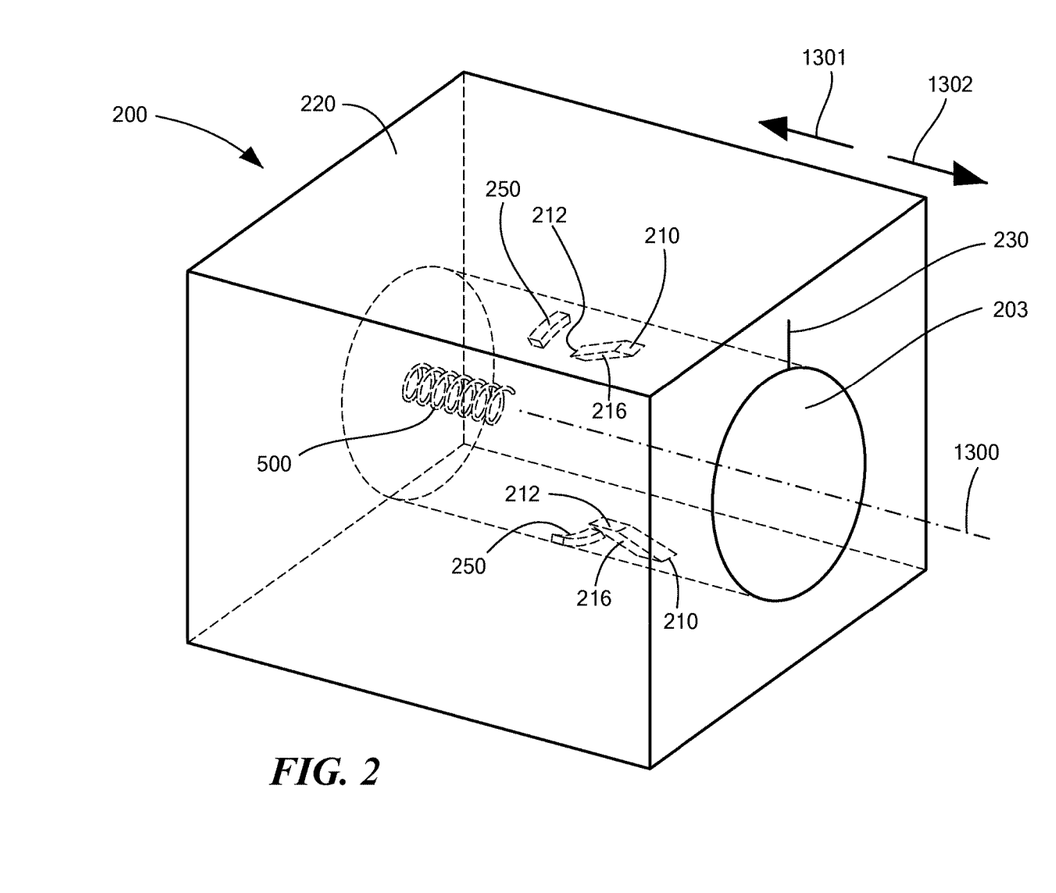
FIG. 2 is a perspective view of another component usable with the component of FIG. 1.

Bore 203 has a first open end 201 to receive male element 100. The opposite end of the bore is closed. Bore 203 also has a plurality of fingers 210 mounted along its inner circumferential surface. Fingers 210 are aligned in the axial directions 1301, 1302 and spaced at equal intervals in the circumferential direction around the axis 1300. Only two fingers 210 are depicted in FIG. 2 for clarity of illustration. As shown, finger 210 is biased by its own resilience in a radially inward direction toward axis 1300.

Each finger 210 has two side edges 216 facing in opposite circumferential directions, a fixed end attached to the inner circumferential surface of bore 203, and a catch end 212 pointing in the forward axial direction 1301. Catch end 212 is dimensioned to engage depression 110 of male element 100 when male element 100 is inserted into the bore 203 of female element 200. Side edges 216 of finger 210 are substantially parallel to one another and are dimensioned to engage with side walls 116 of depression 110, as discussed below. Accordingly, the width of each finger 210 is slightly smaller than the width of each depression 110.

A set of one or more markings 230 on female element 200 are provided at one or more positions on the female element around open end 201. Markings 230 are disposed in predetermined positions relative to fingers 210 in the circumferential direction around axis 1300. For example, each marking 230 may be disposed in alignment with one of the fingers 210 in the circumferential direction around the axis 1300. As discussed below, markings 230 on female element 200 are used in conjunction with markings 130 on male element 100 to bring the elements to a desired rotational alignment relative to one another. Furthermore, female element 200 has a spring 500 that is mounted within bore 203 and designed to engage with male element 100. Spring 500 biases male element 100 in the rearward axial direction 302 when the elements 100,200 are in a range of positions, such as the locked and over advanced positions.

Additionally, female element 200 has electrical contacts 250 disposed on the inner circumferential surface of bore 203. Electrical contacts 250 on female element 200 are designed to engage with electrical contacts 150 on male element 100 when the elements 100,200 are in the locked position. The contacts on the female element typically are electrically connected to other elements (not shown).

Figure 3:
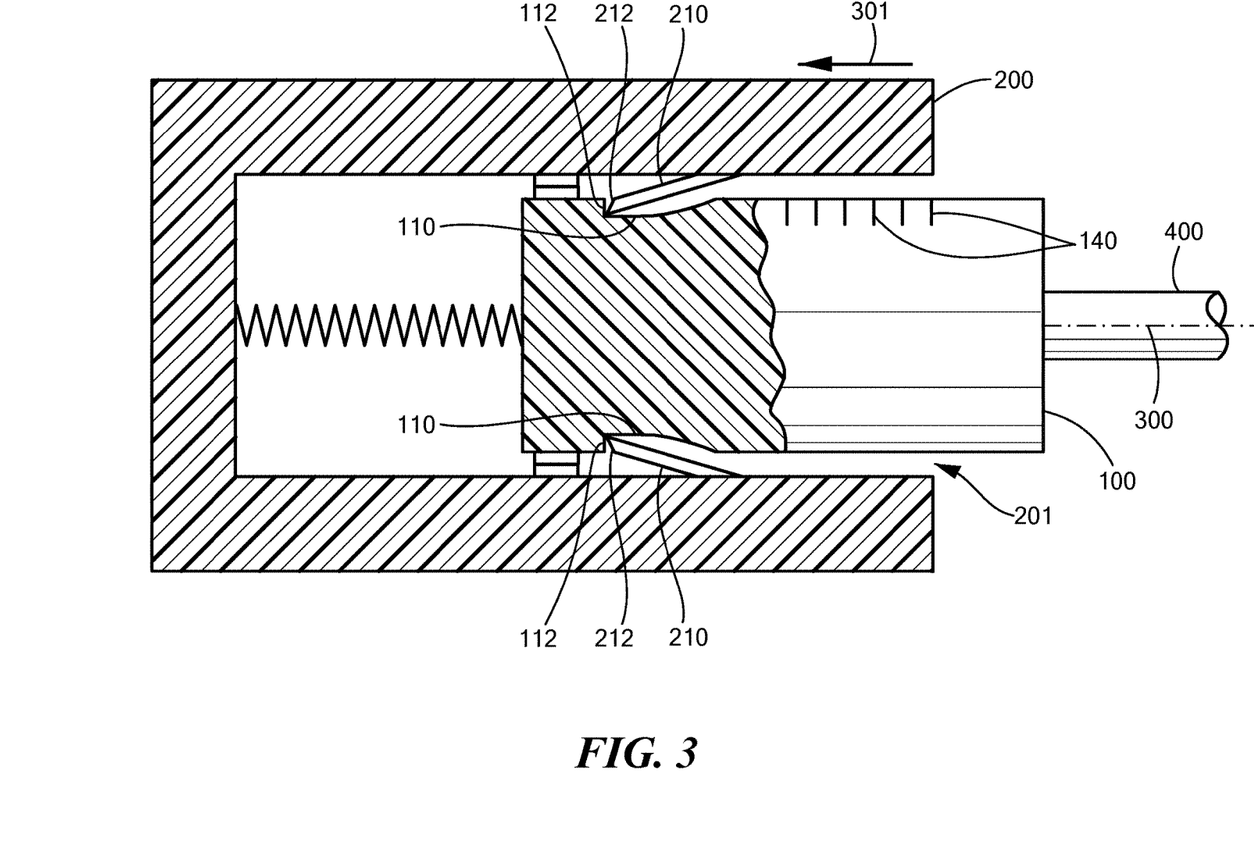
FIG. 3 is a sectional view of the component of FIG. 1 and the component of FIG. 2 in a locked position.

In operation, in a method according to an embodiment of the present disclosure, male element 100 can be slidably inserted in the forward axial direction 301 through the first open end 201 of bore 203 of female element 200. During this step, the male and female elements are rotationally aligned with one another so that bring markings 130 are offset from markings 230, which indicates that each finger 210 is aligned with a depression 110. Although FIG. 3 depicts a radial clearance between the male and female elements for clarity of illustration, in practice these elements desirably fit closely to maintain the elements coaxial with one another. During insertion, fingers 210 are displaced outwardly from the position shown in FIG. 2 as the catch ends 212 ride along circumferential surface 101 of male element 100. Male element 100 advances in the forward or first axial direction 301 through bore 203 until the catch end 212 of each finger 210 engages with depression 110.

When fully engaged, catch end 212 of finger 210 abuts catch wall 112 of depression 110 such that the elements 100,200 are in a locked position wherein the male element 100 cannot move in the rearward or second axial direction relative to the female element 200 (FIG. 3). Thus, catch end 212 and catch wall 112 are self-locking to block movement of male element 100 in the rearward axial direction 302.

In the locked position, depicted in FIG. 3, spring 500 biases male element 100 in the rearward axial direction 302 to keep catch end 212 abutted against catch wall 112. This reinforces the self-locking properties of catch end 212 and catch wall 112 and minimizes the risk of accidental disconnection.

Figure 4:
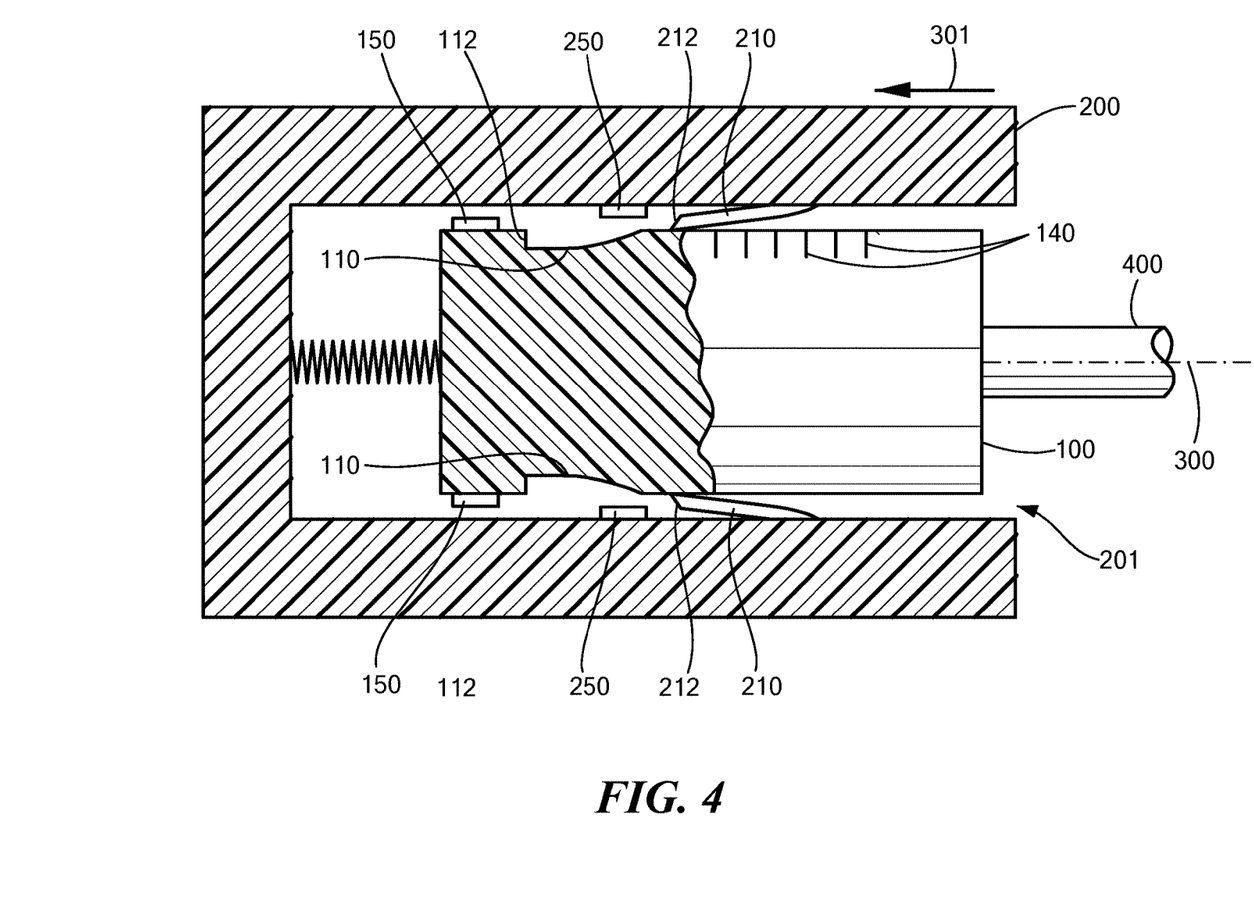
FIG. 4 is a sectional view of the component of FIG. 1 and the component of FIG. 2 in another position, referred to herein as the over advanced position.

Moreover, in the locked position, side edges 216 of finger 210 engage with the side walls 116 of depression 110. Side edges 216 and side walls 116 are also self-locking to block rotational movement of the male element 100 relative to the female element 200. For disconnection and removal of male element 100, the elements 100, 200 transition from the locked position shown in FIG. 3 to an over advanced position shown in FIG. 4. During the transition, male element 100 is moved in the forward axial direction 301 relative to the female element 200. As male element 100 moves in the forward axial direction 301, the catch end 212 of finger 210 rides along the release wall 114 of depression 110 and onto the first portion of the landing area 107a. When the elements 100,200 are in the over advanced position, the catch end of each engagement finger 210 is disposed on the landing area 107a.

Thus, catch end 212 and release wall 114 are not self-locking and do not block movement of male element 100 in the forward axial direction 301. Spring 500 resists movement of male element 100 in the forward axial direction 301 to prevent accidental movement to the over advanced position. If the male element is accidently pushed forward and then released, the spring returns the male element to the locked position.

The relative alignment of markings 140 and the open end of the bore 201 can be used to determine the axial distance the male element 100 travels to reach the over advanced position from the locked position. For example, the markings 140 may be arranged so that when the last marking is aligned with the open end of the bore 201, the elements are in the over advanced position.

In the next step of the disengagement process, male element 100 is rotated about axis 300 relative to female element 200. This rotation continues until markings 130,230 are aligned, indicating that the catch end 212 of finger 210 is disposed on the second portion of a landing area 107b and aligned with a land bridge 105. At this point, the elements are in the unlocked position.

Then, male element 100 is moved in the rearward axial direction 302 relative to the female element 200. During the rearward axial movement, catch end 212 bears on the land bridge 105 and does not engage depression 110. As such, male element 100 continues to move in the rearward axial direction 302 and eventually exit through the first open end 201 of bore 203.

A connector assembly including elements 100,200 is desirable because it provides a strong and reliable locked connection and it minimizes the risk of accidental disconnection. Male element 100 cannot move in the rearward axial direction 302 when the elements 100,200 are in the locked position. This is, catch end 212 of finger 210 abuts catch wall 112 of depression 110 and the self-locking properties of catch end 212 and catch wall 112 prevent such rearward movement. Male element 100 also cannot rotate when the elements 100,200 are in the locked position due to the self-locking properties of side-edges 216 of finger 210 and side-walls 116 of depression 110.

The disconnect procedure includes elements 100, 200 transitioning from the locked position to the over advanced position, and then to the unlocked position for removal. To reach the over advanced position, male element 100 moves in the forward axial direction 301 in order for finger 210 to disengage depression 110. To reach the unlocked position, male element 100 rotates about axis 300 until finger 210 is aligned with a land bridge 105.

Figure 5:
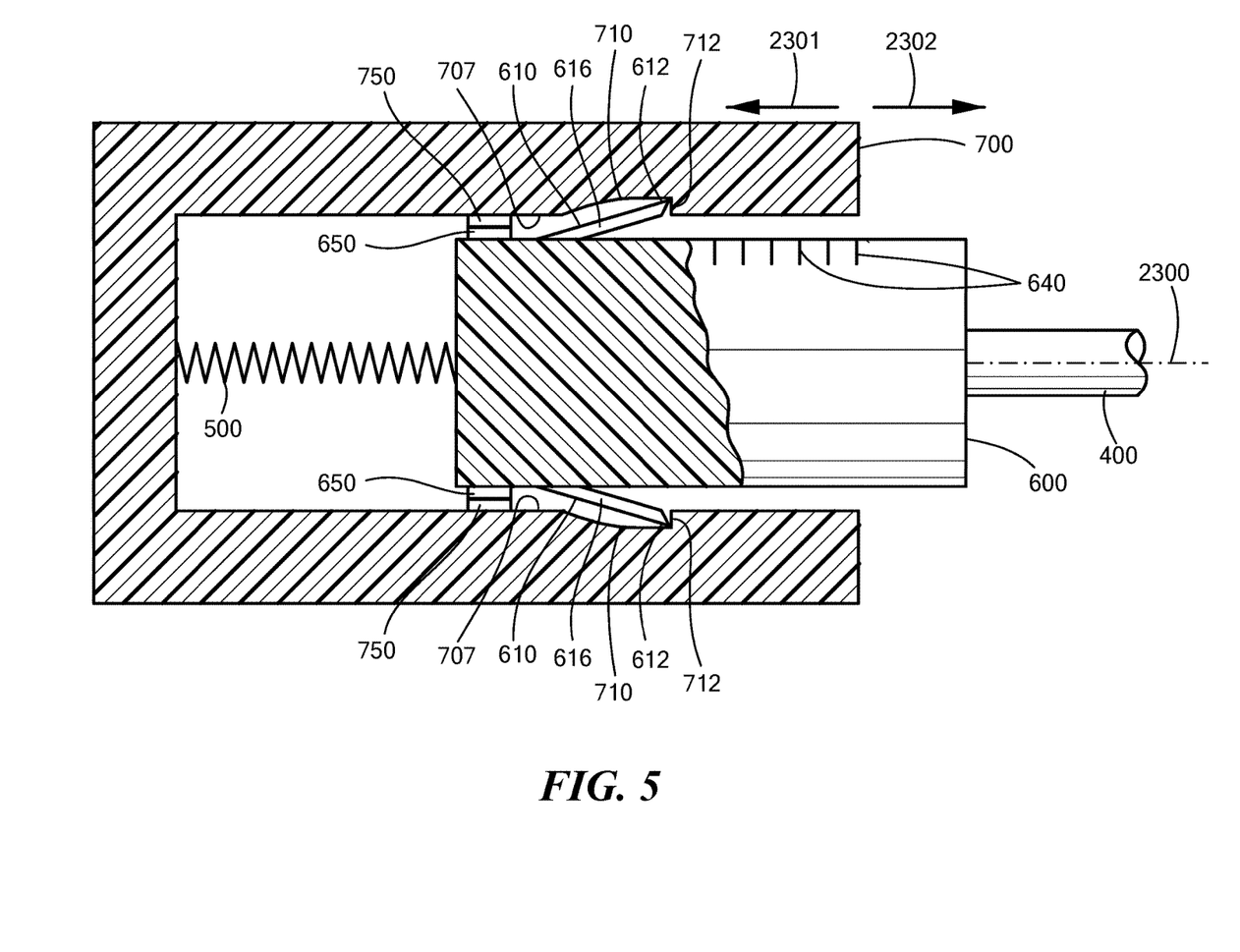
FIG. 5 is a sectional view of two components used in a second embodiment of the present disclosure in a locked position.

The connector assembly according to a second embodiment of the present disclosure (FIG. 5) is similar to the embodiment of FIGS. 1-4 except that in the embodiment of FIG. 5, the fingers are mounted to the male element 600 and the catch ends 612 of the fingers 610 engage depressions 710 in a circumferential surface of the female element 700. In the second embodiment, the male element 600 has a plurality of fingers 610 disposed around an axis 2300 and the female element 700 has a plurality of depressions 710 along an inner circumferential surface of a bore 703 (not shown). Here again, the axis 2300 has a forward or first axial direction 2301 and a rearward or second axial direction 2302.

Fingers 610 on male element 600 are biased in a radially outward direction away from axis 2300. Each finger 610 has two side edges 616, a fixed end attached to the male element 600, and a catch end 612 pointing in the rearward axial direction 1302. Each finger 610 has side edges 616 of finger 610 facing in opposite circumferential directions. The inner circumferential surface 701 of the female element has an arrangement of depressions, land bridges, and landing areas similar to the arrangement on the male element in FIGS. 1-4 above, but with the axial directions reversed. Thus, the depressions 710 on female element 700 are interspersed with plurality of land bridges (not shown) in the circumferential direction. Each depression 710 has two side walls (not shown), a catch wall 712 facing the forward axial direction 2301, and a release wall 714 facing the rearward axial direction 2302. Landing areas 707 are offset from the depressions 710 in the forward axial direction and disposed adjacent release walls 714.

Female element 700 may further have electrical contacts 750 to engage with electrical contacts 650 on male element 600. Additionally, female element 700 may have a spring 500 mounted within bore 703 (not shown) that engages with the male element 600 and biases the male element 600 in the rearward axial direction 2302.

In operation, the same methods for connection and disconnection can be used with the first and second embodiments of the connector assembly. Male element 600 can be slidably inserted into the bore of female element 700. The fingers 610 are displaced inwardly from the position shown in FIG. 5 as the catch ends 612 ride along the inner circumferential surface of the bore of female element 700. Male element 600 advances in the forward axial direction 2301 until finger 610 engages with depression 710.

When fully engaged, catch end 612 of finger 610 abuts catch wall 712 of depression 710 such that the elements 600,700 are in a locked position wherein the male element 600 cannot move in the rearward axial direction relative to the female element 200.

When the male element 600 moves farther in the forward axial direction 2301 to reach the over advanced position, the catch end 612 of finger 610 rides along the release wall 714 of depression 710 onto the landing area 707. In the over advanced position, the male element 600 is rotatable relative to the female element 700. During rotation, the catch end 612 of finger 610 bears on the landing area 707.

When the catch end 612 of each finger 610 is aligned with a land bridge (not shown) of the inner circumferential surface, the elements 600,700 are in the unlocked position. Then, the male element 600 is moved in the rearward axial direction 2302. During the rearward axial movement, the catch end 612 of finger 610 bears on the land bridge 705. Here again, markings (not shown) may be provided on the element to assist the operator in bringing the elements to the unlocked position.

Figure 6B:
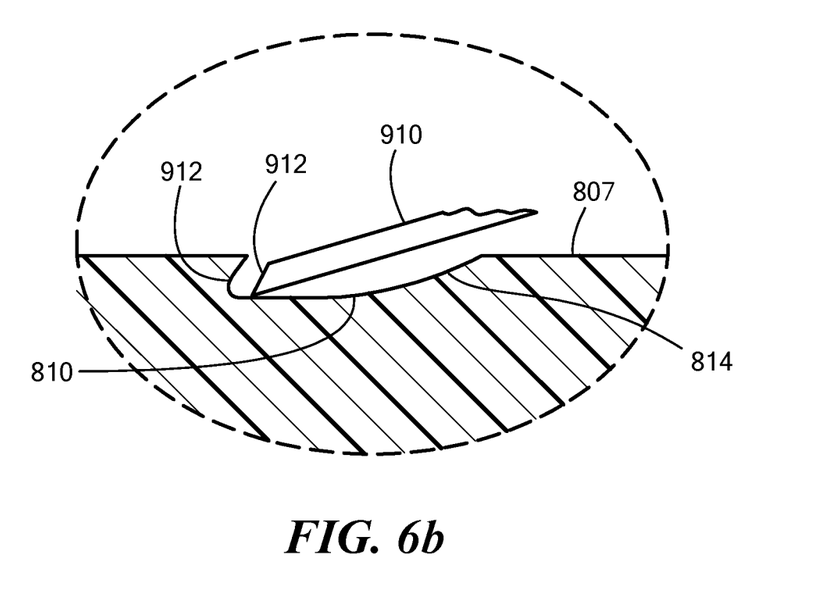
FIGS. 6b-6d are views similar to FIG. 6a but depicting portions of components according to different embodiments of the disclosure.
Figure 6C:
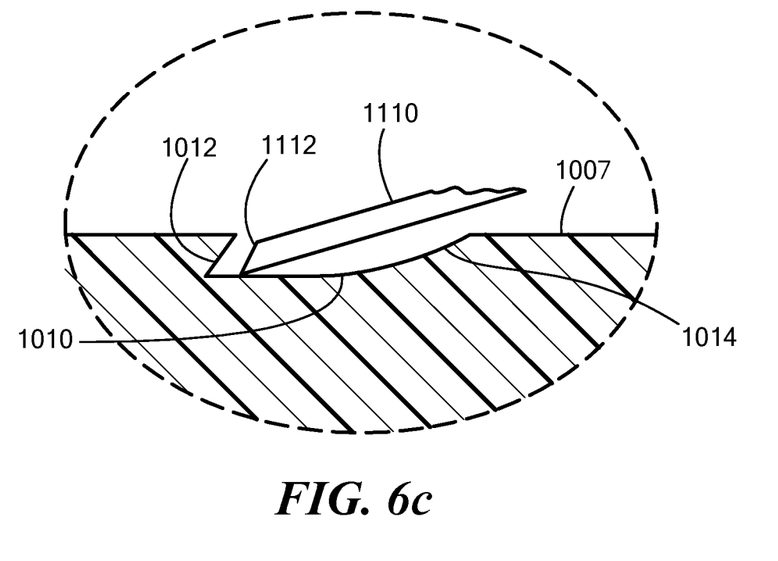
Figure 6D:
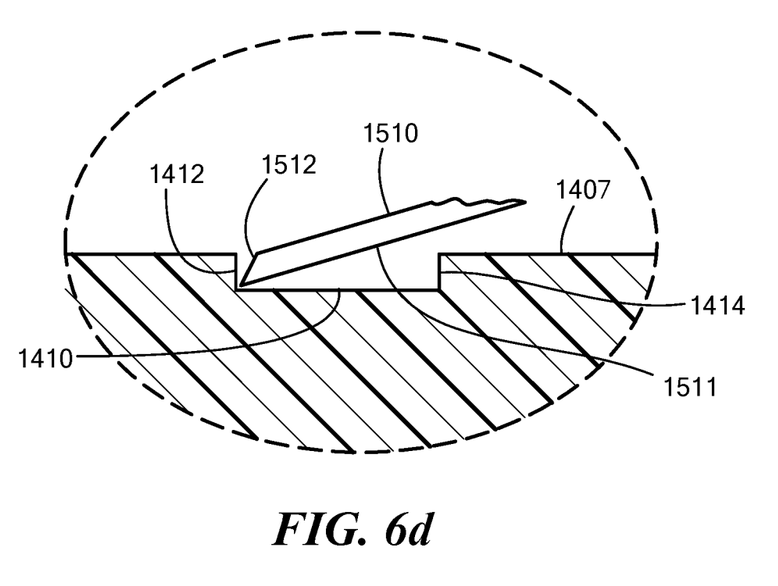

In different embodiments, the catch wall and release wall of the depression may have different shapes and angles (FIGS. 6b-d). For example, the catch wall 812 of depression 810 may be a beveled cliff (FIG. 6b) or the catch wall 1012 of depression 1010 may be a sharp cliff (FIG. 6c). Also, the release wall of the depression need not be sloped. Both the catch wall 1412 and the release wall 1414 of depression 1410 may be substantially perpendicular to the axis (FIG. 6d). As shown in FIG. 6d, where the finger 1510 defines a sloping surface 1511 facing toward the depression, As the elements move toward the over-advanced position, the sloping surface 1511 of the finger bears on the edge of the release wall 1414 and lift the finger out of the depression. There are variable combinations that can be used in other embodiments wherein the catch wall of the depression and the catch end of the finger are self-locking and wherein the release wall disengages the finger from the depression.

Also, in other embodiments, there need not be a plurality of fingers or depressions and they need not be of even number or evenly spaced at regular intervals. It is likely that one finger and one depression would sufficiently prevent movement of the male element in the rearward axial direction. However, the number of fingers and corresponding depressions may affect the strength of the connection between elements and so the recommended embodiment would depend on the application.

Though FIG. 2 shows finger 210 is resilient and biased by its own resilience, this is not required in all embodiments.

For example, each finger may be a rigid element and may be biased by a separate spring, magnet, or other biasing element. FIG. 2 also shows catch end 212 as a pointed tip, but in other embodiments, the catch end of the finger may be a different shape that is dimensioned to engage the catch wall of the depression, for example, the catch end may be a cantilever hook.

In other embodiments, the female element may have a bore with two open ends, rather than one open end. A spring may alternatively be mounted on the male element rather than the female element. Still, the same method for connection and disconnection would be effective as long as the male element is insertable and rotatable relative to the female element.

In the embodiments discussed above, the electrical contacts are mounted on the circumferential surfaces which bear the depressions and fingers. However, this is not essential. Merely by way of example, the male element may include an elongated shaft bearing contacts, the shaft projecting from the body having the depressions or fingers. In still other embodiments, the elements may incorporate stop surfaces which abut one another to arrest forward movement of the male element at the over-advanced position.

Although the disclosure herein has been described with reference to particular embodiments, it is to be understood that these embodiments are merely illustrative of the principles and applications of the present invention.

What is claimed is:

1. A connector assembly, comprising:
   a female element having a bore with an open end;
   a male element insertable into the bore of the female element along an axis in a first axial direction and removable from the bore of the female element in a second axial direction opposite the first axial direction;
   the male element defining a circumferential surface extending around the axis, a depression in the circumferential surface, and a land bridge corresponding to the depression, and the depression having a catch wall facing in one of the group consisting of the first axial direction and the second axial direction and a release wall facing in the other one of the group consisting of the first axial direction and the second axial direction;
   the female element having a finger mounted thereon the finger having a catch end biased in a radial direction transverse to the axis, the catch end of the finger being configured to engage the depression and abut the catch wall to block axial movement of the male element in the second direction relative to the female element when the female element and the male element are in a locked position;
   the male element being movable in the first axial direction relative to the female element to transition from the locked position to an over advanced position, the male element being removable from the bore of the female element by moving in the second axial direction relative to the female element while the male element and the female element are in an unlocked position, the catch end bearing on the land bridge during movement in the second axial direction; the circumferential surface further includes a landing area offset from the depression in an axial direction and disposed adjacent the release wall, the landing area having a first portion aligned with the depression in the circumferential direction and a second portion aligned with the land bridge in the circumferential direction; and
   an electrical contact disposed on the male element and an electrical contact disposed on the female element, the electrical contact on the male element being engaged with the electrical contact on the female element when the elements are in the locked position.

2. The connector assembly of claim 1, wherein the catch end of the finger faces the first axial direction and is biased inwardly toward the axis, the catch wall of the depression faces in the second axial direction, and the release wall of the depression facing in the first axial direction.

3. The connector assembly of claim 1, wherein the circumferential surface includes the land bridge offset from the depression in a circumferential direction around the axis and aligned with the depression in the first and second axial directions.

4. The connector assembly of claim 1, wherein the catch end of the finger is configured to move over the release wall of the depression onto the first portion of the landing area as the male and female elements transition to the over advanced position, and wherein the male and female elements in the over advanced position being rotatable about the axis relative to one another to transition from the over advanced position to an unlocked position in which the catch end is disposed on the second portion of the landing area, the catch end bearing on the landing area during such rotation.

5. The connector assembly of claim 1, wherein the landing area is a part of a surface of revolution around the axis.

6. The connector assembly of claim 1, wherein the circumferential surface is a surface of revolution around the axis.

7. A method for releasing a male element and a female element from a locked position comprising:
   moving the male element within a bore of the female element in a first axial direction to transition from a locked position, in which a finger on one of the group consisting of the male element and the female element is engaged with a depression on the other one of a group consisting of the male element and the female element and blocks movement of the male element in a second axial direction opposite the first axial direction, to an over advanced position, the movement in the first axial direction dislodges the finger from the depression and positions the finger on a landing area on the other one of the group consisting of the male element and the female element;
   rotating one of the group consisting of the male element and the female element relative to the non-rotated one of the group consisting of the male element and the female element to transition from the over advanced position to an unlocked position, the rotation moves the finger out of rotational alignment with the depression and aligns the finger with a land bridge on the other one of the group consisting of the male element and the female element, the finger bearing on the landing area during rotation, the landing area having a first portion aligned with the depression in a circumferential direction and a second portion aligned with the land bridge in the circumferential direction; and
   moving the male element within the bore of the female element in the second axial direction, the finger bearing on the land bridge as the finger moves past the depression.

8. The method of claim 7, wherein the female element includes a spring biasing the male element in the second axial direction when the female element and the male element are in the locked position.

9. The method of claim 7, further comprising determining an axial distance of the male element with respect to the bore and whether the male element and the female element are in the over advanced position based on the plurality of markings.

10. The method of claim 7, wherein the male element defines an axis extending therethrough, the axis defining the first axial direction and the second axial direction, and wherein the male element includes a circumferential surface extending around the axis.

11. The method of claim 10, further comprising rotating one of the group consisting of the male element and the female element relative to the other one of the group consisting of the male element and the female element about the axis to transition from the over advanced position to the unlocked position.

12. The method of claim 11, further comprising rotating one of the male and female elements relative to the other male and female elements about the axis until a marking on the male element is aligned with a marking on the female element.

13. A connector assembly, comprising:
a female element including a housing defining a bore having an open end and an axis extending through the open end, the axis defining a first axial direction and a second axial direction opposite the first axial direction and a finger including a catch end extending from the housing in a radial direction transverse to the axis;
a male element insertable into the bore of the female element and movable along the axis,
the male element defining a circumferential surface extending around the axis and a depression in the circumferential surface, the depression having a catch wall facing in one of a group consisting of the first axial direction and the second axial direction, the circumferential surface of the male element defining:
a land bridge offset from the depression in a circumferential direction around the axis and aligned with the depression in the first axial direction and the second axial direction; and
a landing area having a first portion aligned with the depression in the circumferential direction and a second portion aligned with the land bridge in the circumferential direction, and the depression includes a release wall opposite the catch wall; and
a locked position including the catch end of the finger of the female element contacting the catch wall of the male element.

14. The connector assembly of claim 13, wherein the locked position is configured to block axial movement of the male element in the second axial direction relative to the female element.

15. The connector assembly of claim 13, wherein the male element includes a landing area defined by the circumferential surface, and the landing area is sized to receive the catch end of the finger thereon.

16. The connector assembly of claim 13, wherein the catch end of the finger of the female element is movable relative to the release wall of the depression, and wherein the male element is rotatable around the axis relative to the female element.

17. The connector assembly of claim 13, wherein the female element and the male element each include an electrical contact engageable with each other.

* * * * *